United States Patent [19]
Linker

[11] Patent Number: 4,996,439
[45] Date of Patent: Feb. 26, 1991

[54] COPLANARITY INSPECTION MACHINE
[75] Inventor: Frank V. Linker, Springfield, Pa.
[73] Assignee: American Tech Manufacturing, Corp., Glenolden, Pa.
[21] Appl. No.: 427,797
[22] Filed: Oct. 27, 1989
[51] Int. Cl.⁵ ............................................. G01N 21/86
[52] U.S. Cl. ....................................... 250/561; 33/645
[58] Field of Search .............. 250/561, 230; 29/566.3, 29/721; 356/381, 376; 33/533, 560, 645

[56] References Cited
U.S. PATENT DOCUMENTS 3,278,023 10/1966 Schneider ........................... 250/230
4,739,175 4/1988 Tamura ............................... 250/561
4,774,768 10/1988 Chiponis ............................. 33/533
4,814,621 3/1989 Soth et al. .......................... 250/561

Primary Examiner—David C. Nelms
Assistant Examiner—Que Tan Le
Attorney, Agent, or Firm—Eugene E. Renz, Jr.

[57] ABSTRACT

A signal device for operation on a path including a movable reflector aligned to move along an axis and a light source and light detector positioned to provide a signal trip point when light from the source is reflected by the reflector to the detector at a predetermined location on said axis.

32 Claims, 3 Drawing Sheets

COPLANARITY INSPECTION MACHINE

FIELD OF THE INVENTION

The present invention relates to a coplanarity inspection machine and more particularly to a device for determining coplanarity of multiple lead devices such as those used in the electronics industry.

BACKGROUND OF THE INVENTION

Many objects are so fragile that contacting them at all subjects them to damaging stress. Some fragile surfaces, however, can withstand a light force and therefore can be subjected to direct measurement in which contact occurs.

This ability to contact fragile objects is of particular importance in the manufacture of semi-conductor packages which are applied to the surface of a printed circuit board. When a plurality of leads extend from a single device, it often times is necessary to determine if all of the leads are appropriately arranged for contact on the printed circuit board. Particularly when multiple leads extend in the same direction, so that the device is mounted on the surface of the printed circuit board and is suspended above the board by the leads, it is necessary that these leads all make contact with the surface of the PC board. It is particularly important to have complete contact with all of the leads since each lead is essential for the total functionality of the device.

Nevertheless, there is no conventional measurement means to determine whether or not all of the leads of a surface mounted device (SMD) are in the same plane, so that appropriate and effect contact with the surface of the printed circuit board can be achieved. Linear probes and micrometers have not been successful in achieving the degree of accuracy needed for error free manufacturing. Also, use of these inadequate methods as described above can often times cause more of the individual leads to be non-aligned and therefore causes more problems than it solves.

Presently, non-contacting calibration methods are employed in which lasers are aligned to measure an absolute distance. However, these designs require very careful alignment and are extremely expensive as well. A totally automated system using a laser would be prohibitively expensive. It would be a great advantage to the art if a device could be provided which would allow contacting the various leads of a SMD prior to mounting it on a printed circuit board to determine that all of the leads are within the required degree of coplanarity. In this manner, the mounting of the SMD would be highly reliable and effective during automated assembly of the completed device.

With the foregoing in mind, it is an object of the present invention to provide a method for accurately determining the coplanarity of the individual leads in a SMD.

Another object of the present invention is to provide a device which is suitable for accurately measuring deviations of various points in a plane from a coplanarity of that plane.

Still another object of the present invention is to provide a device which can automatically display the location of individual leads on an SMD which are outside of an acceptable limit for coplanarity.

Yet another object of the present invention is to provide a signal device for use for with SMD and other sensitive or fragile articles of manufacture.

SUMMARY OF THE INVENTION

It has now been discovered that the above and other objects of the present invention can be accomplished in the following manner. Specifically, a signal device has been discovered for operation on a path in order to generate a signal. The device includes a movable reflector means which is aligned to move along that path. Also included is a light source and a light detector positioned to provide a signal when light from the source is reflected by the reflector to the detector at a predetermined location on the path.

In one embodiment of the present invention, the device described above may be moved along said path both by an object and a reference object, so as to provide a signal and a reference signal for comparison there between. A plurality of such devices can be used to provide a plurality of signals, in one case generated by a reference plane and in the other case by various points on an object to be measured, so that the coplanarity of the object can be determined.

When specifically designed for determining the coplanarity of multiple lead devices, such as SMDs, the device includes a means for providing a set of signals upon intersection with individual leads of the SMD as the SMD is moved along a linear axis. A reference set of signals is also provided upon intersection upon corresponding points in a known plane which is moved along that axis, such as with a gage means. In addition, there is a means for identifying the deviation between the signal from each lead and the corresponding reference signal from the plane, to thereby identify the deviation of each lead from coplanarity.

In another embodiment, the device is provided for determining coplanarity of a multiple lead device. A linear motion means is provided for moving a multiple lead device such as an SMD along a linear axis. Particularly preferred are gull wing lead devices and "J" lead devices. A gage means is also provided, having a known plane with points thereon corresponding to the various leads on the multiple lead device. The gage means and the multiple lead device are adapted to move along the axis by the linear means. A signal means is positioned at a fixed location along that axis for providing a set of signals when contacted by each of the leads indicating the lead position on that axis and also providing a reference set of signals when contacted by corresponding points on the plane carried or defined by the gage means in order to indicate the position of those points on that axis. Finally, comparator means are provided for comparing the signal with the reference signal for each lead and the corresponding point in the plane, in order to identify the deviation of each lead from coplanarity.

In a specific embodiment of the present invention, the device for determining coplanarity of a multiple lead device includes a plurality of tines which are fixably mounted at one end and have a movable or free other end. A signal means is associated with each of the tines and is adapted to generate a signal upon contact and deflection of the individual lead with which it is associated. A linear motion means is provided to transport a multiple lead device along a linear axis which is generally perpendicular to the plane of the leads. A gage means defining a known plane having points thereon corresponding to the individual leads of the multiple lead device is also provided. The gage means is adapted to move along the axis using the linear motion means and intersect the tines. Comparator means are provided for comparing the reference signal when each tine is deflected upon movement of the gage means along the axis with the signal generated when each tine is deflected by a lead of the multiple lead device moved along that axis. The comparator will then identify the deviation of each lead from a coplanarity.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

As is noted, it would be highly desirable to measure the contacting surfaces of the leads of semi-conductor packages at the point where they will make contact with the surface of the printed circuit board. This measurement is expressed as the coplanarity of the leads. It is desirable in the eyes of many electronic equipment manufacturers to use surface mounting procedures for multi-leaded electronic packages rather through hole mounting. Surface mounting requires extreme accuracy of the coplanarity of the leads to ensure that proper solder wicking takes place.

In its simplest form, the present invention employs a switch or signal generating device which recognizes the arrival of the leads from an electronic surface mounted device (SMD) and compares the arrival location with the location of a standardized or reference plane. The difference of location on the axis between the lead and corresponding point on the reference plane indicates the degree of coplanarity.

In its simplest form, the preferred switch of the present invention comprises a thin tine made of spring material which is secured or clamped at one end and is suspended over a pair of fiber optic conductors. The fiber optic conductors have one end connected to an emitter and the other to a detector. The two fiber optic conductors are placed in a manner as to provide a beam of light to reflect off of the tine at its free end, at a predetermined angle, wherein the light is picked up by the detector fiber optic conductor.

A linear motion encoder is used to locate the position of the various objects being moved along the path for intersection of the tine. As the SMD leads move into the tines, the linear encoder records the trip point at which each tine causes a change in the reflective signal to be sent through the fiber optic conductors. Prior to this, a reference point corresponding to the individual lead was measured by moving a flat gage block which has been manufactured to have a known coplanarity.

Figure 1:
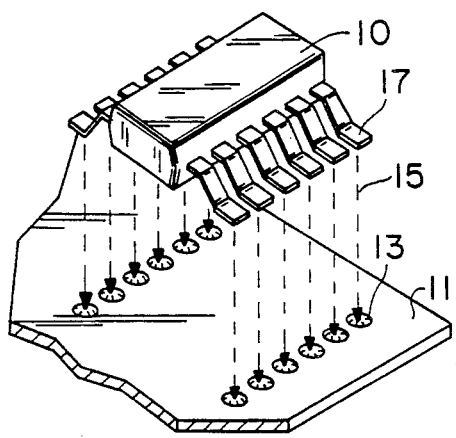
FIG. 1 is an exploded perspective view illustrating a gull wing surface mount device above a fragmentary portion of a PC board.

As shown in FIG. 1, a surface mounted device 10 is to be mounted on a PC board 11 by contacting with solder dots 13. The SMD 10 is lowered in the direction of arrows 15 until the leads 17 contact the solder dots 13 and connection is made.

Figure 2:
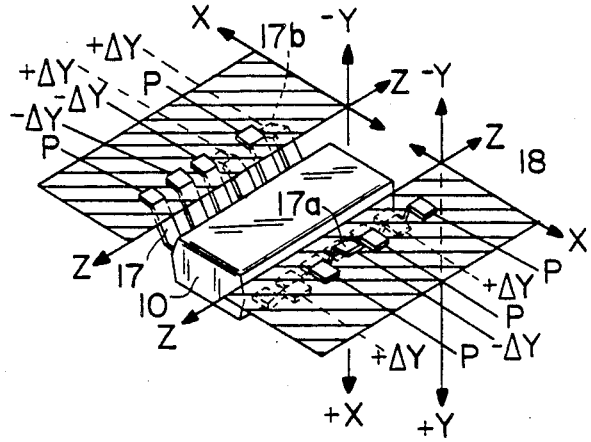
FIG. 2 is a perspective schematic view illustrating an SMD similar to that shown in FIG. 1, but shown in an inverted position and illustrating a non-coplanarity of the leads.

Shown in FIG. 2 is the SMD 10 of FIG. 1 with varying leads 17. These leads 17 are shown as gull wing leads, although other lead shapes such as "J" wing leads are equally applicable for the present invention. The particular style of lead and the particular electronics of the SMD are not part of the present invention, since this invention is operable for all designs.

In FIG. 2, some of the leads 17 are coplaner with the plane 18. In lowering the SMD 10 onto the printed circuit board 11, those leads 17 which are in coplanarity with plane 18 will mate suitably with the solder dots 13 and good connection will be achieved. However, some of the leads 17 are not in the plane 18 but extend out of plane by a distance, as shown by, for example, leads 17a, and 17b, along with the other leads in FIG. 2 as they deviate along the Y axis as shown. In the case of leads such as 17a, which extends further than the plane 18, there is a danger that the SMD 10 will be tilted and other leads will not make adequate contact with the solder dots 13. In the case of leads such as 17b, as shown in FIG. 2, the other leads being in contact with the PC board 11 may prevent the lead 17b from making contact. In either case, a defective assembly has been made.

In order to overcome the deficiencies of the prior art as shown in FIGS. 1 and 2, and to permit the location and correction of deviations in individual leads, the following apparatus has been developed in accordance with the principles of this invention. The SMD 10 is mounted on a linear motion mount 19 which is accurately moved by gear drive 21 back and forth as needed in the direction of double arrow 23. An accurate motor 25 is provided to precisely move the linear motion mount 19.

In the case of a dual sided SMD, such as the SMD 10 shown in FIGS. 1 and 2, the following arrangement is provided. As will be shown herein after, four-sided SMDs and SMDs with J wing leads and other designs are also completely within the scope of the present invention.

Figure 3:
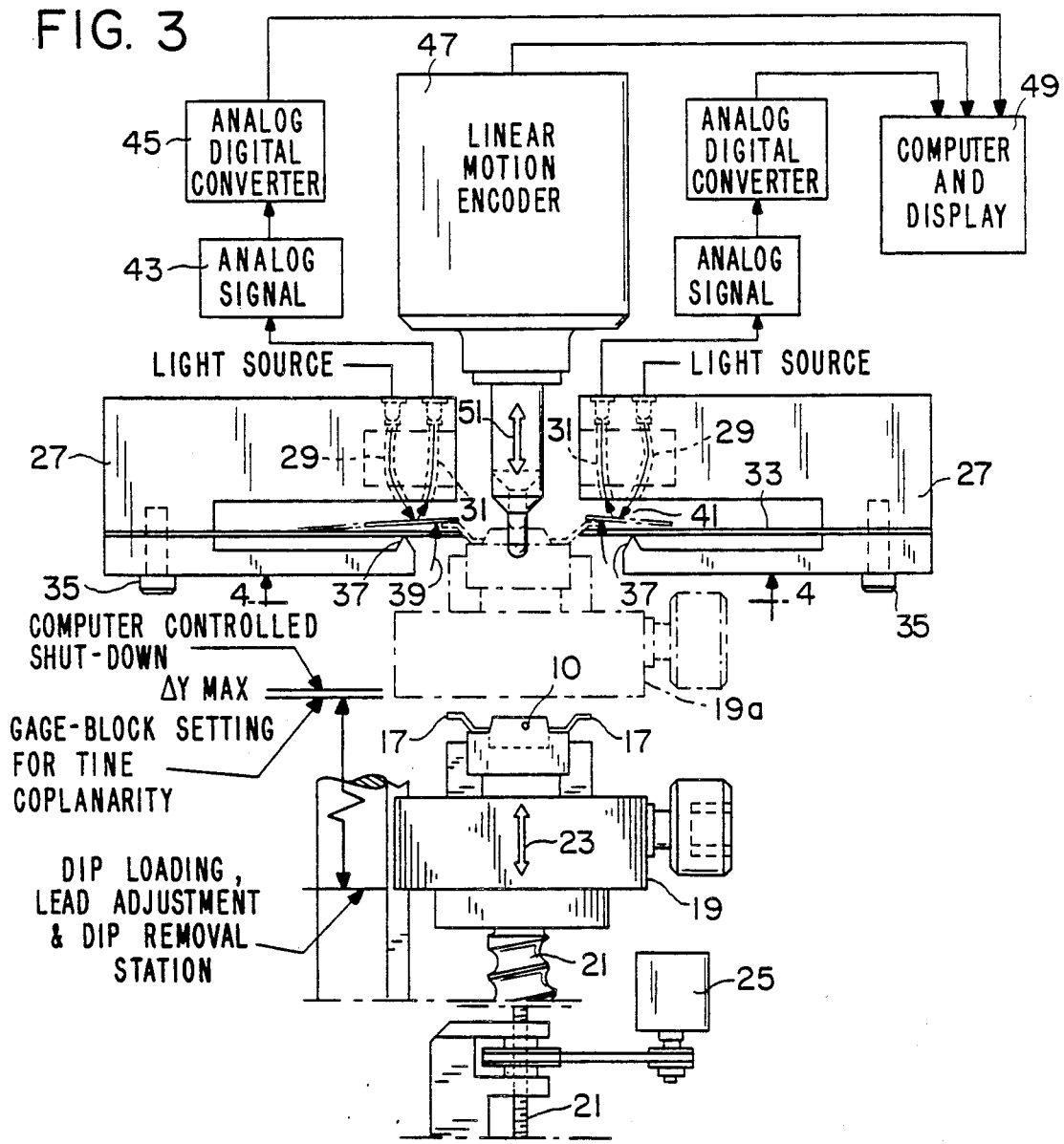
FIG. 3 is a semi-schematic elevational view showing a device for the testing of lead coplanarity of the SMD of FIGS. 1 and 2, all in accordance with the invention.

A beam switch 27 is aligned in FIG. 3 to intersect with the leads 17 on both sides of the SMD 10. The beam switches includes a fiber optic light source 29 and a fiber optic light detector 31. The light from the source 29 reflects off of the metallic tine 33 and returns to the fiber optic detector 31 when the tine 33 is in a predetermined position. The tine 33 is held in the beam switch 27 by fixably mounting the tine 33 at one end, such as by bolt 35. Normally, before the system is in use, the tine 33 is biased at point 37 and it is designed to move in the direction of arrow 39 when subjected to pressure from an object being moved along the axis of arrow 23.

When the linear motion mount 19 brings the leads 17 of the SMD 10 into contact with the tines 33, and reaches the position shown by the linear motion mount, in 19a shown in dot-dash lines, light from the light source travels through fiber optic light source 29 and reflects off of tine 33 as shown by arrows 41, thereby sending a signal to the fiber-optic light detector 31. When this light trip point or change is detected by light detector 31, a signal is sent to the analog signal receiver 43. The analog signal from box 43 is converted in analog to digital convertor 45. The linear motion encoder 47 measures the actual position of the linear motion mount 19 and also provides a signal. The analog to digital signal convertor 45 and the linear motion encoder 47 send signals to computer and display 49.

Figure 4:
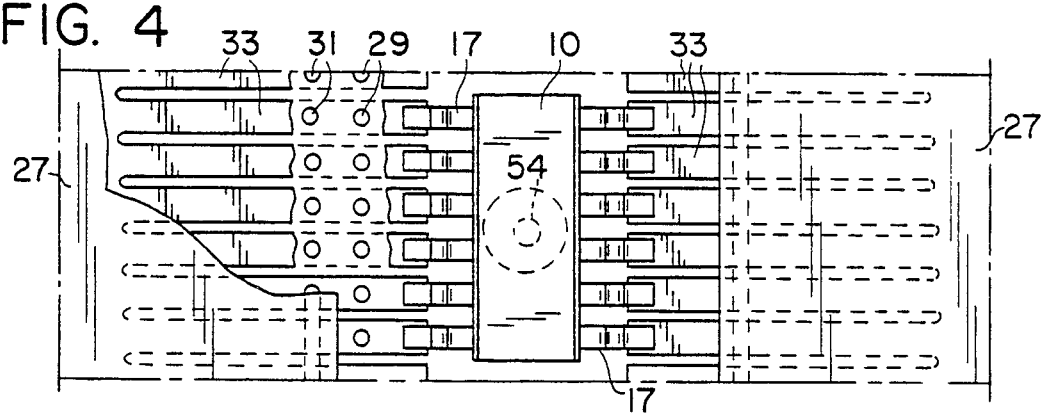
FIG. 4 is a slightly enlarged, fragmentary bottom plan view taken along lines 4—4 of FIG. 3, with some parts broken away to more clearly illustrate certain details of construction.

As shown in FIG. 4, in a slightly enlarged fragmentary bottom plane view taken along lines 4—4 of FIG. 3, with some parts missing, certain detail of the beam switch are shown. Specifically, fiber optic source 29 and detector 31 are shown in alignment with the tines 33 and it is clear from this figure how the individual leads 17 of the SMD 10 contact individual tines 33. In this figure, the gull wing SMD 10 is shown with its associated lead pads 17 in contact with the outermost unsupported terminal ends of the tines 33 of the beam switch 27.

Figure 5:
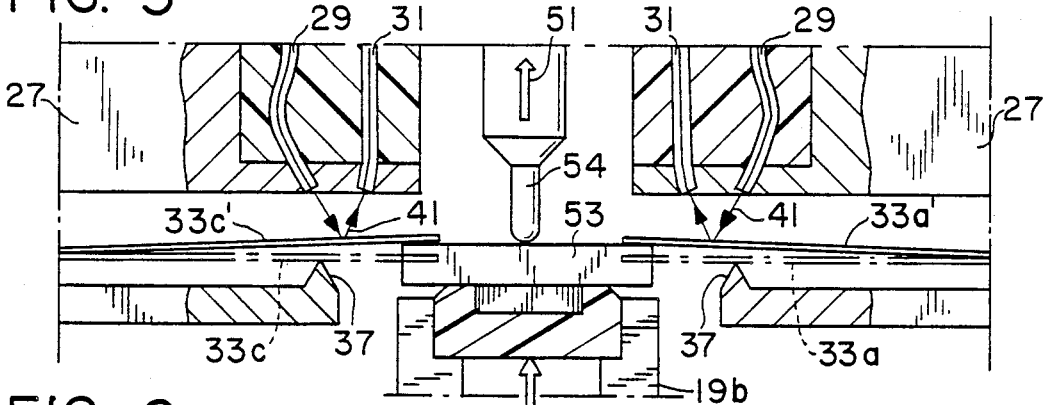
FIG. 5 is an enlarged fragmentary elevational view with portions broken away and in section to show additional detail of one embodiment of this invention, showing a reference gage being used.

In FIG. 5, the upper end 19b of the linear motion mount 19 has been moved forward in the direction of arrow 51 until the gage block 53 has intersected the various tines 33a and 33c, for example. Initially, as was shown in FIG. 3, the tines 33a and 33b are resting on pivot points 37. As the plane of the gage block 53 engages tines 33a and 33c, they are moved along the direction of the path, as shown by arrow 51, until the light from fiber optic light source 29 impinges on the tine 33a' or 33c' at a point where it reflects back to the fiber optic detector 31. At this point, as each of the many tines 33 in the unit reflect light through the light source 29 and detector 31, reference points are placed in the computer memory. Since the gage block 53 is carefully machined to have a true plane surface, the point at which each tine 33 in the total device causes a signal to be generated by reaching the point of reflectance, shown by arrow 31, for example, is recorded as a reference signal for that particular tine 33.

Stated another way, each of the individual tines 33 have been deflected by the coplaner surface of the gage block 53 by a distance so that all of the tines fall within the profile of the gage block. In one embodiment, a probe 54 contacts the center of the gage block 53 and records the location in incremental changes, such as every 0.0001 inches. This information is conveyed to the linear motion encoder 47 which generates a signal for each predetermined increment in elevational change of the gage block 53. That information is stored simultaneously with the signal generated as each tine 33 reaches the position on the path of arrow 23 that causes the angular reflection through arrows 41 to issue a signal change.

Figure 6:
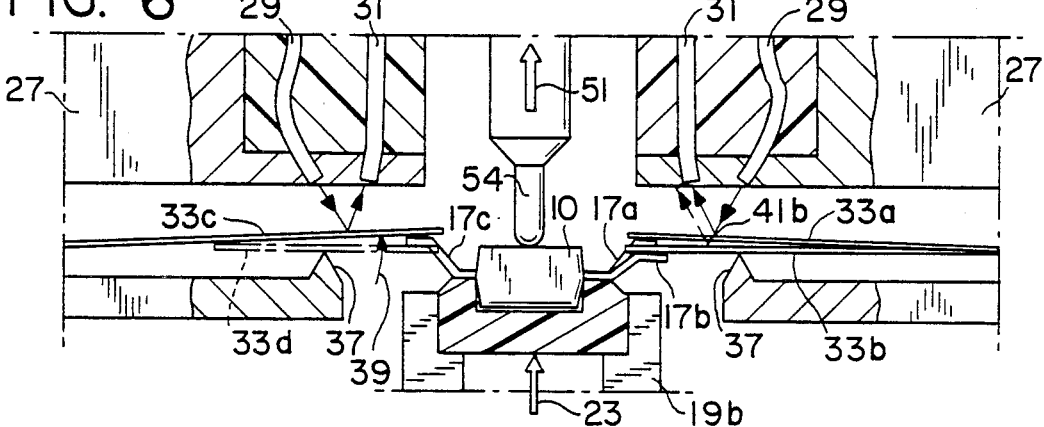
FIG. 6 is an enlarged fragmentary, elevational view similar to FIG. 5, showing a gull wing SMD being tested.

In FIG. 6, the same apparatus is employed, with a SMD device 10 being substituted for the gage block 53. Probe 54 is calibrated to read the same starting point that it did when gage block 53 began travel along the direction of arrow 51. Again, the increments are recorded by the linear motion encoder 47 and those signals are transmitted to the computer and display device 49. In this particular case, the SMD 10 inlcudes, among many other leads, leads 17a, 17b, and 17c. Initially, of course, all of the tines are resting on the pivot point 37. As the SMD 10 travels in the direction of arrow 51, probe 54 notes the linear location. In FIG. 6, lead 17a extends above the coplanarity which is desired. Therefore, lead 17a intersects tine 33a ahead of the rest of the tines. As tine 33a reaches the point when light reflects from the light source 29 to the light detector 31, a signal is sent by the analog signal device 43, to the analog to digital convertor 45 and to the computer. Similarly, a reflection of light from the light source 29 to the light detector 31 indicates the arrival of tine 33 at the proper point, as it is moved in the axial direction of the path 23 by lead 17c. At each time when the signal is sent indicating the arrival of a certain tine at its signal sending location, the linear distance is also recorded. In the case where the lead 17b is not sufficiently coplaner as shown in FIG. 6, the tine 33b will not be deflected from pivot point 37 to permit light source 29 to reflect off tine 33b and impinge upon detector 31. Instead, the light path 41b will not activate detector 31 until a later time. Eventually, subject to limit switches which would prevent damage to the machine, each of the tines 33 will convey a signal as they are interacted by the leads 17.

It is now possible to determine which leads, if any, have deviated from coplanarity by an amount which has been predetermined to be problematic. Specifically, the computer calculates the difference between the actual linear location of the deflection for each lead and compares that location with the reference location which was generated when the gage block intersected the same tines. If the difference in location between the reference value and the actual value is 0, or is within a predetermine acceptable tolerance, coplanarity will have been achieved. If the difference between the signal from an individual tine which has been displaced by a particular lead is greater than the acceptable deviation from the reference signal corresponding to that time, the operator will be notified. In some instances, the SMD is merely rejected. In other more sophisticated systems, the SMD is withdrawn from the contact with the tines, the offending lead is adjusted either up or down depending upon the information which has been determined from the first measurement, and recheck is done. If the adjustment is proper, the lead will now be within the acceptable limits of coplanarity and the device can be passed as an acceptable device. It is within the scope of the individual assembly procedures to determine when and how deviated leads are corrected.

Figure 7:
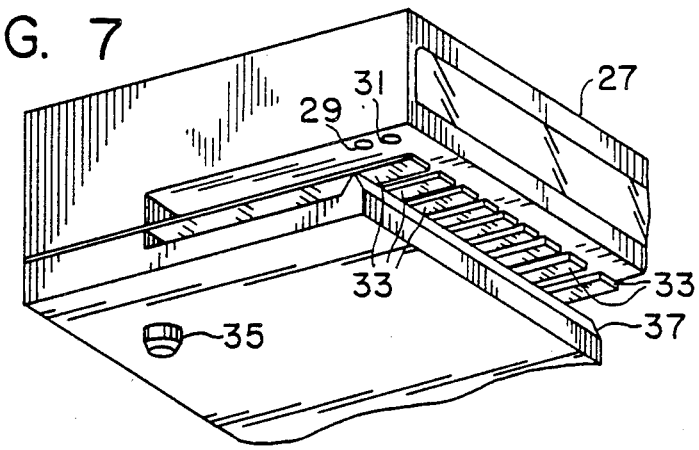
FIG. 7 is a fragmentary perspective view illustrating the physical design of one embodiment of this invention.

As shown in FIG. 7, a perspective view of the beam switch 27 includes a plurality of tines 33 and individual fiber optic light sources 29 and light detectors 31. The pivot point 37 forms part of the mounting structure, as the fixed ends of the tines 33 are held to the beam switch via bolt 35. The number of tines 33 is determined by the number of leads on the devices being measured for coplanarity.

Figure 8:
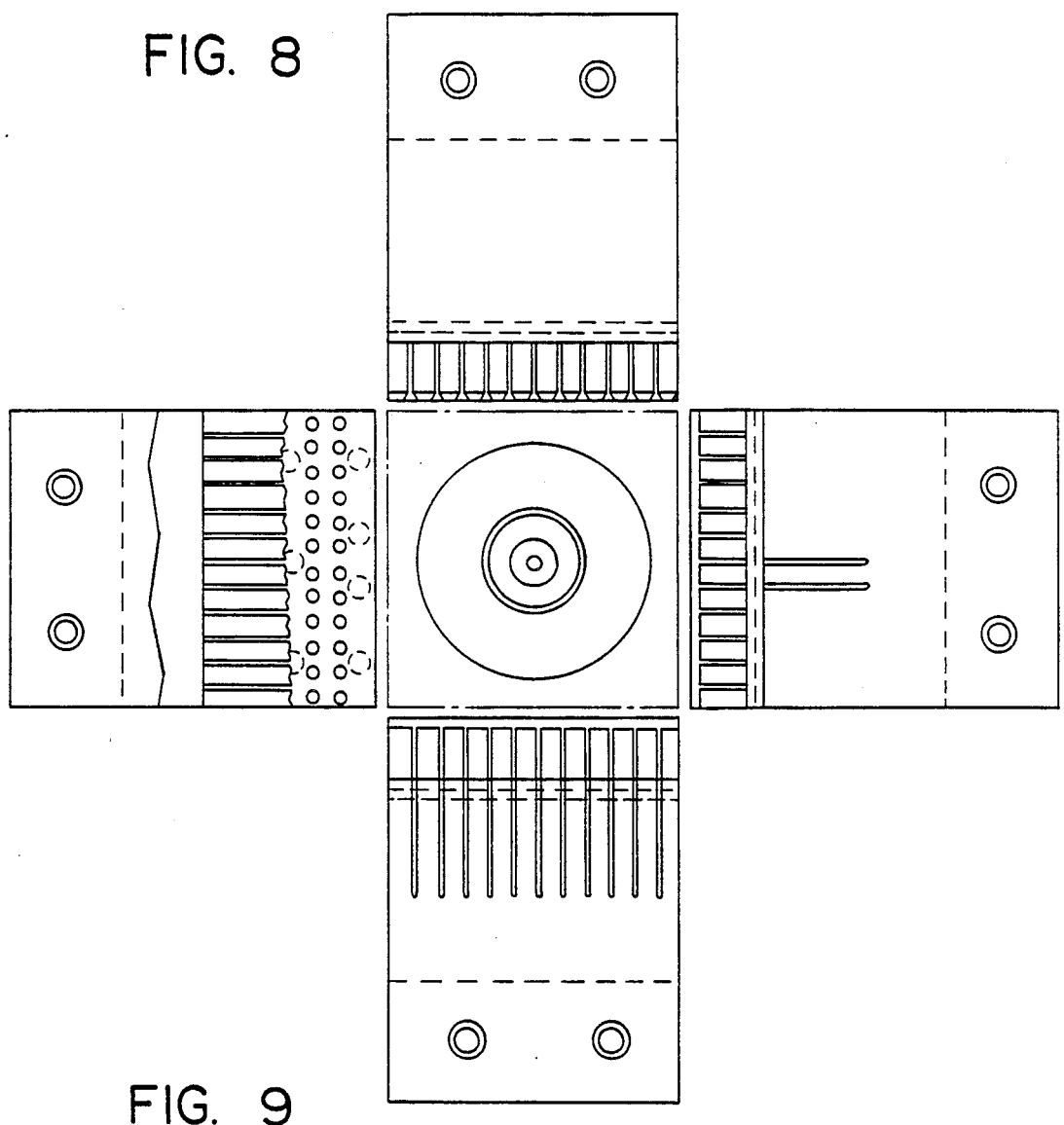
FIG. 8 is a bottom plan view illustrating a modified arrangement of the device shown in the above figures, in which the coplanarity of a square of four-sided SMD is evaluated.

As shown in FIG. 8, there is a bottom plane view illustrating a modified arrangement of the beam switches shown above. Specifically, four sets of beam switches evaluate the coplanarity of square SMDs having leads extending from all four side walls. In SMDs of this type, it is particularly important that the coplanarity be achieved, not only because the number of leads has been maximized, but also because deviant leads can have a material effect on all of the remaining leads. The principle of operation is the same, however, no matter how many leads are depending from the SMD. As each lead deflects its own individual tine 33, causing the switching effect of light transmission from light input 29 to light detector 31, the location of that lead is determined with respect to the reference value when that same tine is contacted by a standard or a reference gage block. In this manner, the difference between the reference signal and the actual location of the individual lead is calculated. Deviation from the reference standard defines the amount of coplanarity.

Figure 9:
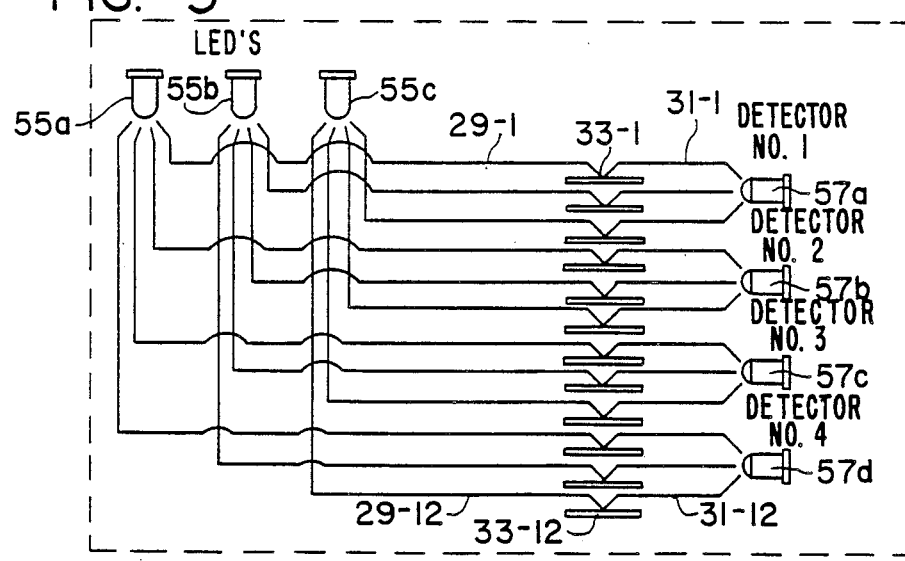
FIG. 9 is a schematic view illustrating a multiplexing arrangement for increasing the number of individual points of measurement in the preferred embodiment of the present invention.

As can be seen from FIG. 8, the number of fiber optic light sources and detectors is fixed or determined by the number of tines, which in turn are fixed by the number of leads being evaluated for coplanarity. It has been discovered, however, that it is not necessary to provide individual light sources or detectors for each optical fiber. As shown in FIG. 9, three light emitting diodes, 55a, 55b, and 55c are used to each provide a light source to four fiber optic light sources 29-1 through 29-12. Thus, three light sources provide light for 12 optical fibers. These 12 optical fibers 29-1 through 29-12 operates on individual tines 33-1 through 33-12 and provide a signal at the appropriate time to the fiber optic detectors 31-1 through 31-12. Each of these fiber optic detectors 31-1 through 33-12 provide a signal to one of four detectors 57a, 57b, 57c and 57d. The timing of the signals from the emitters 55 can be communicated through the microprocessor or the computer along with the data from the four detectors 57. Thus, the detector 57a will be able to determine which of the three light emitting diodes 55a through 55c transmitted the signal which is received at any point in time. As can be seen, this allows for miniaturization and eliminates space requirements for a number of light sources and photo detectors. Programming the computer to distinguish between the various light sources and detectors is, of course, straight forward.

What is claimed is:

1. A signal device for operation on a path, comprising:
 a moveable reflector aligned to move along said path;
 a light source and light detector positioned to provide a signal when light from source is reflected by said reflector to said detector at a predetermined location on said path; and
 comparator means for comparing the location on said path of separate signals from an object and a reference object on said path.

2. The device of claim 1 wherein said movable reflector is fixedly mounted at one end and has a free end aligned to move along said path.

3. A method of generating a signal on a path comprising the steps of:
 moving a movable reflector aligned to move along said path;
 positioning a light source and light detector to provide a signal when light from said source is reflected by said reflector to said detector at a predetermined location on said path; and
 comparing the location on said path of separate signals from an object and a reference object on said path.

4. The device of claim 1 which includes a plurality of sets of reflectors, light sources and detectors to provide a plurality of signals.

5. The device of claim 4 wherein said plurality of sets are aligned on said path to give a plurality of signals in a plane.

6. The device of claim 1 wherein said object is a multiple lead device.

7. The device of claim 6 wherein said object comprises a multiple lead device having a plurality of leads, each of which leads is aligned to contact one of said set of reflectors.

8. The device of claim 7 wherein said reference object is a gage means defining a known plane having points thereon corresponding to said leads.

9. A device for determining coplanarity of multiple lead devices, comprising:
 signal means for providing a set of signals upon intersection with individual leads of a multiple lead device as the device is moved along a linear axis and providing a reference set of signals upon intersection of corresponding points in a known plane moved along said axis; and
 comparitor means for identifying the deviation between a signal from each lead and the corresponding reference signal from said plane, to thereby identify the deviation of each lead from coplanarity.

10. The device of claim 9, wherein said signal means includes a movable reflector aligned to move along said axis and a light source and light detector positioned to provide a signal when light from said source is reflected by said reflector to said detector at a predetermined location on said axis.

11. The device of claim 10 wherein said movable reflector is fixedly mounted at one end and has a free end aligned to move along said axis.

12. The device of claim 10 wherein said reflector is moved along said axis separately by an object and a reference object, to provide a signal and a reference for comparison therebetween.

13. The device of claim 10 which includes a plurality of sets of reflectors, light sources and detectors to provide a plurality of signals.

14. A device for determining coplanarity of a multiple lead device, comprising:
 linear motion means for moving a multiple lead device along a linear axis; gage means defining a known plane having points thereon corresponding to said leads, said gage means being adapted to move along said axis by said linear means;
 signal means at a fixed location along said axis for providing a set of signals when contacted by each lead to indicate the position of that lead along said axis and providing a reference set of signals when contacted by said corresponding points on said plane to indicate the position of those points along said axis; and
 comparator means for comparing said signals with said reference signals for each lead and the corresponding point in said plane to identify the deviation of each lead from coplanarity.

15. The device of claim 14, wherein said signal means include a movable reflector aligned to move along said axis and a light source and light detector positioned to provide a signal when light from said source is reflected by said reflector to said detector at a predetermined location on said axis.

16. The device of claim 15 wherein said movable reflector is fixedly mounted at one end and has a free end aligned to move along said axis.

17. The device of claim 15 wherein said reflector is moved along said axis separately by an object and a reference object, to provide a signal and a reference signal for comparison therebetween.

18. The device of claim 15 which includes a plurality of sets of reflectors, light sources and detectors to provide a plurality of signals.

19. The device of claim 18 wherein said plurality of sets are aligned on said axis to give a plurality of signals in a plane generally perpendicular to said path.

20. The device of claim 19 wherein said set of reflectors are moved along said axis separately by an object and a reference object, to provide a signal and reference signal for comparison therebetween.

21. A device for determining the coplanarity of a multiple lead device, comprising:
a plurality of tines fixably mounted at one end and having a free end;
signal means associated with each of said tines and adapted to generate signal upon deflection of each tine;
linear motion means for transport of a multiple lead device along a linear axis;
gage means defining a known plane having points thereon corresponding to said leads, said gage means being adapted to move along said axis by said linear means; and
comparator means for comparing the reference signal when each tine is deflected upon movement of said gage means along said axis with the signal generated when each tine is deflected by a lead of said multiple lead device moved along said axis, to thereby identify the deviation of each lead from coplanarity.

22. The device of claim 21, wherein said signal means includes a movable tine aligned to move along said axis and a light source and light detector positioned to provide a signal when light from said source is reflected by said tine to said detector at a predetermined location on said axis.

23. The device of claim 22 wherein tine reflector is moved along said axis separately by an object and a reference object, to provide a signal and a reference signal for comparison therebetween.

24. A method for determining coplanarity of multiple lead devices, comprising the steps of:
providing a set of signals upon intersection with individual leads of a multiple lead device as the device is moved along a linear axis;
providing a reference set of signals upon intersection of corresponding points in a known plane moved along said axis; and
identifying the deviation between a signal from each lead and the corresponding reference signal from said plane, to thereby identify the deviation of each lead from coplanarity.

25. The method of claim 24, wherein said signals are generated by light from a source being reflected by a reflector to a detector at a predetermined location on said axis.

26. A method for determining coplanarity of a multiple lead device, comprising the steps of:
moving a multiple lead device along a linear axis;
defining a known plane having points thereon corresponding to said leads by moving a gage means along said axis, providing a set of signals by contacting each lead to indicate the position of that lead along said axis and providing a reference set of signals by contacting corresponding points on said plane to indicate the position of those points along said axis; and
comparing said signals with said reference signals for each lead and the corresponding point in said plane to identify the deviation of each lead from coplanarity.

27. The method of claim 26, wherein said signals are generated by a reflector aligned to move along said axis and a light source and light detector positioned to provide a signal when light from said source is reflected by said reflector to said detector at a predetermined location on said axis.

28. The method of claim 27 wherein said signals are generated by a movable reflector which is fixedly mounted at one end and has a free end aligned to move along said axis.

29. A method for determining the coplanarity of a multiple lead device, comprising the steps of:
mounting a plurality of tines fixedly at one end and having a free end;
generating a signal upon deflection of each tine;
transporting a multiple lead device along a linear axis;
defining a known plane with a gage means having points thereon corresponding to said leads by moving said gage means along said axis; and
comparing the reference signal when each tine is deflected upon movement of said gage means along said axis with the signal generated when each tine is deflected by a lead of said multiple lead device moved along said axis, to thereby identify the deviation of each lead from coplanarity.

30. The method of claim 3 wherein said movable reflector is fixedly mounted at one end and has a free end aligned to move along said path.

31. The method of claim 3 which includes providing a plurality of sets of reflectors, light sources and detectors to generate a plurality of signals.

32. The method of claim 31 wherein said plurality of sets are aligned on said path to give a plurality of signals in a plane generally perpendicular to said path.

* * * * *